(12) United States Patent
Mansouri-Ruiz (10) Patent No.: US 6,814,727 B2
(45) Date of Patent: Nov. 9, 2004

(54) AUTOMATIC/MANUAL LONGITUDINAL POSITION TRANSLATOR AND ROTARY DRIVE SYSTEM FOR CATHETERS

(75) Inventor: Idriss Mansouri-Ruiz, Santa Clara, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 284 days.

(21) Appl. No.: 09/970,314

(22) Filed: Oct. 2, 2001

(65) Prior Publication Data

US 2002/0072704 A1 Jun. 13, 2002

Related U.S. Application Data

(63) Continuation of application No. 09/130,198, filed on Aug. 5, 1998, now Pat. No. 6,319,227.

(51) Int. Cl.[7] .............................................. A61M 25/16
(52) U.S. Cl. ........................ 604/535; 604/528; 600/463; 606/170
(58) Field of Search ............................ 604/22, 523, 528, 604/533, 534, 535; 606/159, 167, 170; 600/433, 434, 445, 463, 466, 585, 467

(56) References Cited

U.S. PATENT DOCUMENTS

| | | |
|---|---|---|
| 4,794,931 A | 1/1989 | Yock |
| 4,841,977 A | 6/1989 | Griffith et al. |
| 4,870,970 A | 10/1989 | Gray et al. |
| 4,887,606 A | 12/1989 | Yock et al. |
| 4,917,097 A | 4/1990 | Proudian et al. |
| 4,951,667 A | 8/1990 | Markowitz et al. |
| 5,000,185 A | 3/1991 | Yock |
| 5,024,234 A | 6/1991 | Leary et al. |
| 5,049,130 A | 9/1991 | Powell |
| 5,211,176 A | 5/1993 | Ishiguro et al. |
| 5,358,485 A | 10/1994 | Vance et al. |
| 5,485,846 A | 1/1996 | Webler et al. |
| 5,524,630 A * | 6/1996 | Crowley ............... 600/466 |
| 5,544,660 A * | 8/1996 | Crowley ............... 600/466 |
| 5,546,947 A | 8/1996 | Yagami et al. |
| 5,759,153 A | 6/1998 | Webler et al. |
| 5,797,858 A | 8/1998 | Rourke |
| 5,827,313 A | 10/1998 | Ream |
| 5,865,748 A | 2/1999 | Co et al. |

FOREIGN PATENT DOCUMENTS

WO  WO 92/03095  3/1992

* cited by examiner

Primary Examiner—Michael J. Hayes
(74) Attorney, Agent, or Firm—Townsend and Townsend and Crew LLP (57) ABSTRACT

An automatic pullback catheter system (2) includes a disposable catheter assembly (6) mountable to a drive assembly (4). The drive assembly includes a body (8) to which a drive chassis (14) is mounted for movement along a longitudinal path (16) by a motor (20) which rotates a longitudinal drive screw (22) selectively coupled to the drive chassis by a threaded clamp (24). A rotary drive motor (30), mounted to the drive chassis, rotates a first combined connector (34). The catheter assembly includes a hollow sheath (38) housing a rotatable and axially movable cable assembly (44). The sheath includes a proximal hub (42) mountable to the body. The cable assembly includes an elongate imaging cable (46) with a second combined connector (36) at its proximal end. The first and second combined connectors are blind matable connectors and provide for the longitudinal movement coupling, the rotary movement coupling and the data/information connection of the two connectors.

9 Claims, 6 Drawing Sheets

AUTOMATIC/MANUAL LONGITUDINAL POSITION TRANSLATOR AND ROTARY DRIVE SYSTEM FOR CATHETERS

This application is a continuation of Ser. No. 09/130,198 filed Aug. 5, 1998 now U.S. Pat. No. 6,319,227.

CROSS-REFERENCE TO RELATED APPLICATIONS

This is related to U.S. patent application Ser. No. 09/074,064, filed May 7, 1998, now U.S. Pat. No. 6,004,271 and entitled "Combined Motor Drive and Automatic Longitudinal Position Translator for Ultrasonic Imaging System"; U.S. patent application Ser. No. 08/721,433 filed Sep. 27, 1996, now U.S. Pat. No. 5,957,941 and entitled "Catheter System and Drive Assembly Thereof"; U.S. patent application Ser. No. 08/722,325 filed Sep. 27, 1996, now U.S. Pat. No. 5,827,313 and entitled "Device for Controlled Longitudinal Movement of an Operative Element Within a Catheter Sheath and Method"; and U.S. Pat. No. 5,361,768, issued Nov. 8, 1994 and entitled "Automated Longitudinal Position Translator for Ultrasonic Positioning Probes, and Method of Using Same".

BACKGROUND OF THE INVENTION

The present invention relates generally to catheters systems. In particular, the present invention is directed to a catheter system that provides for the controlled longitudinal movement of an elongate element—such as a rotatable imaging core with an ultrasonic transducer or an optical fiber imaging device at its distal end, or a drive cable with an atherectomy cutter at its distal end—housed within a sheath positioned within a patient.

Arteriosclerosis, also known as atherosclerosis, is a common human ailment arising from the deposition of fatty-like substances, referred to as atheromas or plaque, on the walls of blood vessels. Such deposits occur in both peripheral blood vessels which feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma, and other devices that are pushed or pulled along or through a deposit, such as atherectomy where a blade or cutting bit is used to sever and remove the atheroma, spark gap reduction in which an electrical spark burns through the plaque, laser angioplasty where laser energy is used to ablate at least a portion of the atheroma, and opening of vessels through the use of stents.

Two major difficulties in using such devices are maintaining a constant translational rate for the device and obtaining images of and information on the region of the blood vessel to be treated. Several imaging techniques have been proposed. Catheters incorporating mechanical rotation of ultrasonic transducers for imaging are disclosed in U.S. Pat. Nos. 4,794,931; 5,000,185; 5,049,130; and 5,024,234. These catheters scan in a plane normal to the catheter axis. Catheters employing phased array imaging systems are disclosed in U.S. Pat. Nos. 4,841,977 and 4,917,097. Catheters employing fiber optic imaging components are also known.

Generally deposits extend some longitudinal distance along the length of a vessel. To view different portions of the deposit a physician typically moves a handle attached to a proximal end of the imaging catheter along the vessel, for example, by pushing or pulling the catheter.

Imaging using computer-assisted reconstruction algorithms enables physicians to view a representation of the patient's interior intravascular structures in two or three dimensions (i.e., so-called three-dimensional or longitudinal view reconstruction). In this connection, image reconstruction algorithms typically employ data-averaging techniques which assume that the intravascular structure between an adjacent pair of data samples will simply be an average of each such data sample. Thus, the algorithms use graphical "fill in" techniques to depict a selected section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

Even with the most skilled physician, it is practically impossible to manually exercise sufficiently slow constant rate longitudinal translation of the ultrasound imaging device (which thereby provides for a precisely known separation distance between adjacent data samples). In addition, with manual translation, the physician must manipulate the translation device while observing the conventional two-dimensional sectional images. This division of the physician's attention and difficulty in providing a sufficiently slow constant translation rate can result in some diagnostic information being missed. To minimize the risk that diagnostic information is missed, it is necessary to lengthen the imaging scan time which may be stressful to the patient. Similarly, it is difficult for physicians to manually control the translational rate of atherectomy catheters and other interventional devices that are longitudinally advanced and retracted through blood vessel and other body lumens.

U.S. Pat. No. 5,485,846 discloses an ultrasound imaging transducer which is capable of being translated longitudinally within a section of a patient's vascular system at a precise constant rate through the use of a longitudinal translation assembly. The longitudinal translation assembly moves the entire rotary drive assembly to provide the desired longitudinal movement of the transducer. Such an ability enables a series of precisely separated data samples to be obtained thereby minimizing (if not eliminating) distorted and/or inaccurate reconstructions of the ultrasonically scanned vessel section (i.e., since a greater number of more closely spaced data samples can reliably be obtained). Also, such an assembly can be operated in a "hands-off" manner which allows the physician to devote his or her attention entirely to the real-time images with the assurance that all sections of the vessel are displayed. While such a longitudinal translation assembly can work well, it is relatively large, bulky and heavy; it is expensive; and it is cumbersome to set up, in part because the rotary drive and longitudinal translation assemblies are wrapped in separate sterile drapes (plastic bags) for sterility.

One drawback with conventional catheter imaging systems is the cost of replacing the disposable catheter assembly. The catheter assembly is mounted to a draped pullback assembly for use, used and then discarded after use. However, the catheter assembly includes the electronics necessary to send, receive and filter signals. These electronic components are disposed of with the rest of the catheter assembly which raises the cost of the procedure.

SUMMARY OF THE INVENTION

The present invention provides an automatic pullback catheter system in which costly electronic signal processing components can be removed from the disposable catheter assembly and incorporated into the drive assembly. This helps reduce the cost of each use. With the present invention, the catheter assembly need only include the sheath, the elongate operative element within the sheath, the drive connector, and the data/information connector, typically a coaxial electrical connector. The drive and data/information connectors are preferably combined into a combined connector. The resulting structure is compact, simple to use, and reduces the cost of the disposable catheter assembly.

The drive assembly includes a body to which a drive chassis is mounted for movement along a longitudinal path by a longitudinal driver. The longitudinal driver typically includes a motor which rotates a longitudinal drive screw selectively coupled to the drive chassis by a threaded clamp or clutch. The drive assembly also includes a rotary driver mounted to the drive chassis and movable with the drive chassis along the longitudinal path. The rotary driver includes a rotary drive motor and a first combined connector rotatable by the rotary drive motor.

The catheter assembly includes a hollow sheath housing an elongate operative element, typically a rotatable imaging core or cable having an imaging element at its distal end. The sheath includes a proximal portion removably mounted to the body. The catheter assembly also includes a rotatable and axially movable second combined connector connected to the proximal end of the cable or other operative element. The second combined connector is preferably housed within the proximal portion of the sheath.

The first and second combined connectors are preferably blind matable connectors to facilitate mounting the catheter assembly to and dismounting the catheter assembly from the drive assembly. The combined connectors provide for the transfer of information/data from the operative element to the drive assembly as well as for both the longitudinal movement coupling of the two combined connectors and the rotary movement coupling of the two combined connectors. Therefore, rotating the first combined connector by the rotary drive motor mounted to the drive chassis rotates the second combined connector thereby rotating the elongate operative element. Likewise, actuating the longitudinal driver drives the drive chassis along the longitudinal path which causes the longitudinal movement of the operative element within the sheath.

The drive chassis is preferably mounted to the body along a linear bearing. Using a linear bearing helps to ensure that the longitudinal movement of the drive chassis is smooth, encounters little friction and is very stable. Using a manually actuated threaded clamp to selectively secure the drive chassis to the longitudinal drive screw permits the user to decouple the drive chassis from the longitudinal drive shaft when desired and manually move the drive chassis, and thus the imaging element at the distal end of the imaging core, to the desired longitudinal position.

Another advantage of the invention results when the connection between the first and second combined connectors is a blind matable connection. That is, the connectors need only be properly aligned so pushing the two connectors together causes them to properly mate. Preferably, the data/information connection is made using coaxial plug and socket connectors which not only provide the desired electrical, optical or other type of connection, but also provides sufficient frictional engagement between the first and second combined connectors to permit the longitudinal movement of the elongate operative element (e.g. cable) within the sheath. While the frictional engagement between the two data/information connectors may be enough to provide an acceptable rotary drive interface, it is preferred that the first and second combined connectors include first and second rotary drive connectors including rotary drive surfaces. These rotary drive surfaces are preferably arranged to guide the two connectors into proper rotary alignment when engaged.

The proximal portion of the cable is preferably much stiffer than the remainder of the cable. This helps to ensure a fluid-tight seal can be provided between the cable and the proximal portion of the sheath. This is important when a fluid or flush port is provided distally of such seal; the seal helps to prevent the fluid from entering into the drive assembly. In addition, this stiff, proximal portion can be made sufficiently long so that when the rotary driver is in the longitudinally pulled-back or proximal position, only the stiff proximal portion of the cable is exterior of the sheath and inside the drive assembly. The stiff portion of the cable is stiff enough to be self-supporting and does not droop within the drive assembly. Pushing the cable distally is also facilitated by the use of a cable with a stiff proximal portion.

Other features and advantages will appear from the following description in which the preferred embodiment has been set forth in detail in conjunction with the accompanying drawings.

DESCRIPTION OF THE PREFERRED EMBODIMENT

Figure 1:
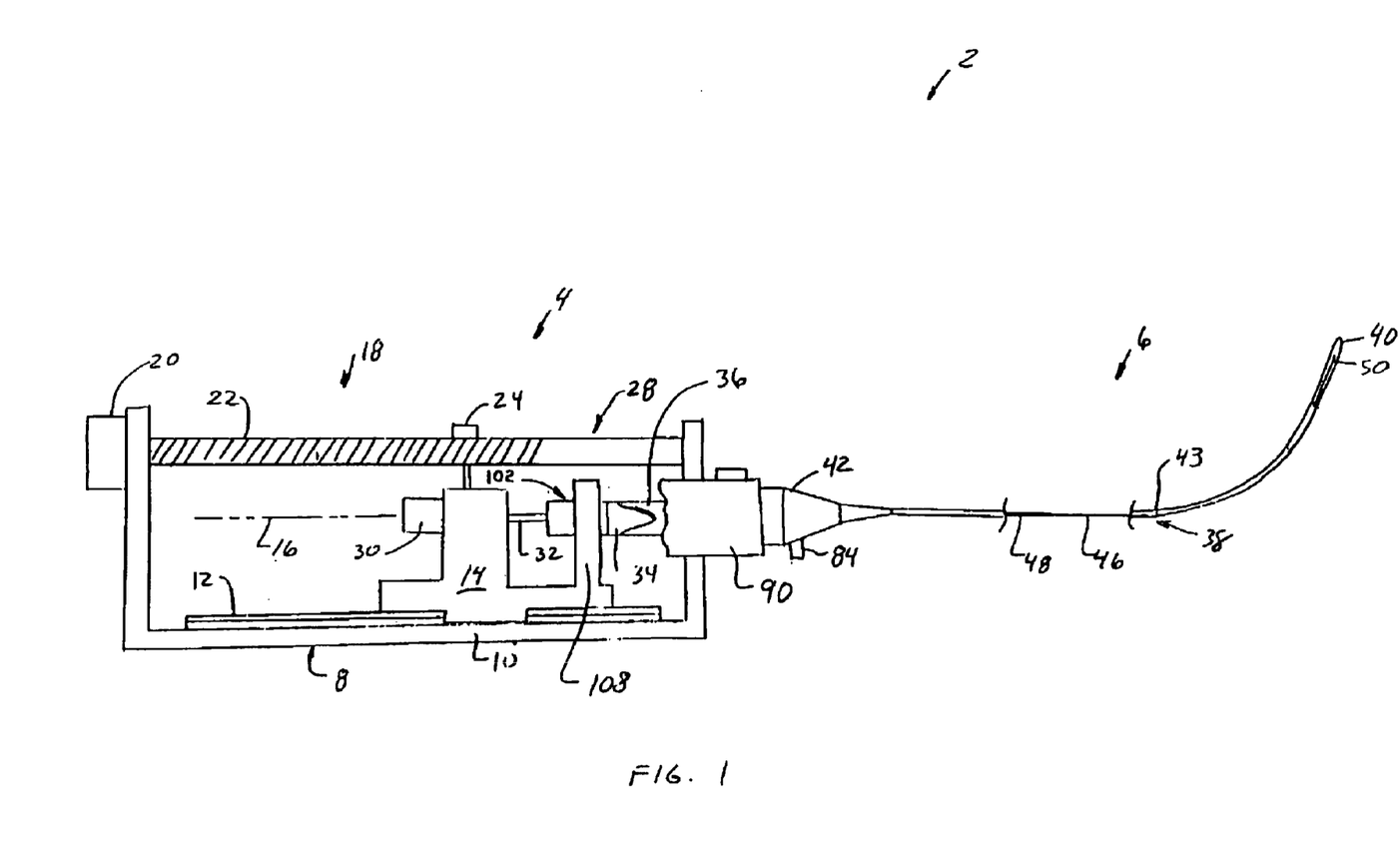
FIG. 1 is a simplified schematic view of a catheter system made according to the invention.
Figure 2:
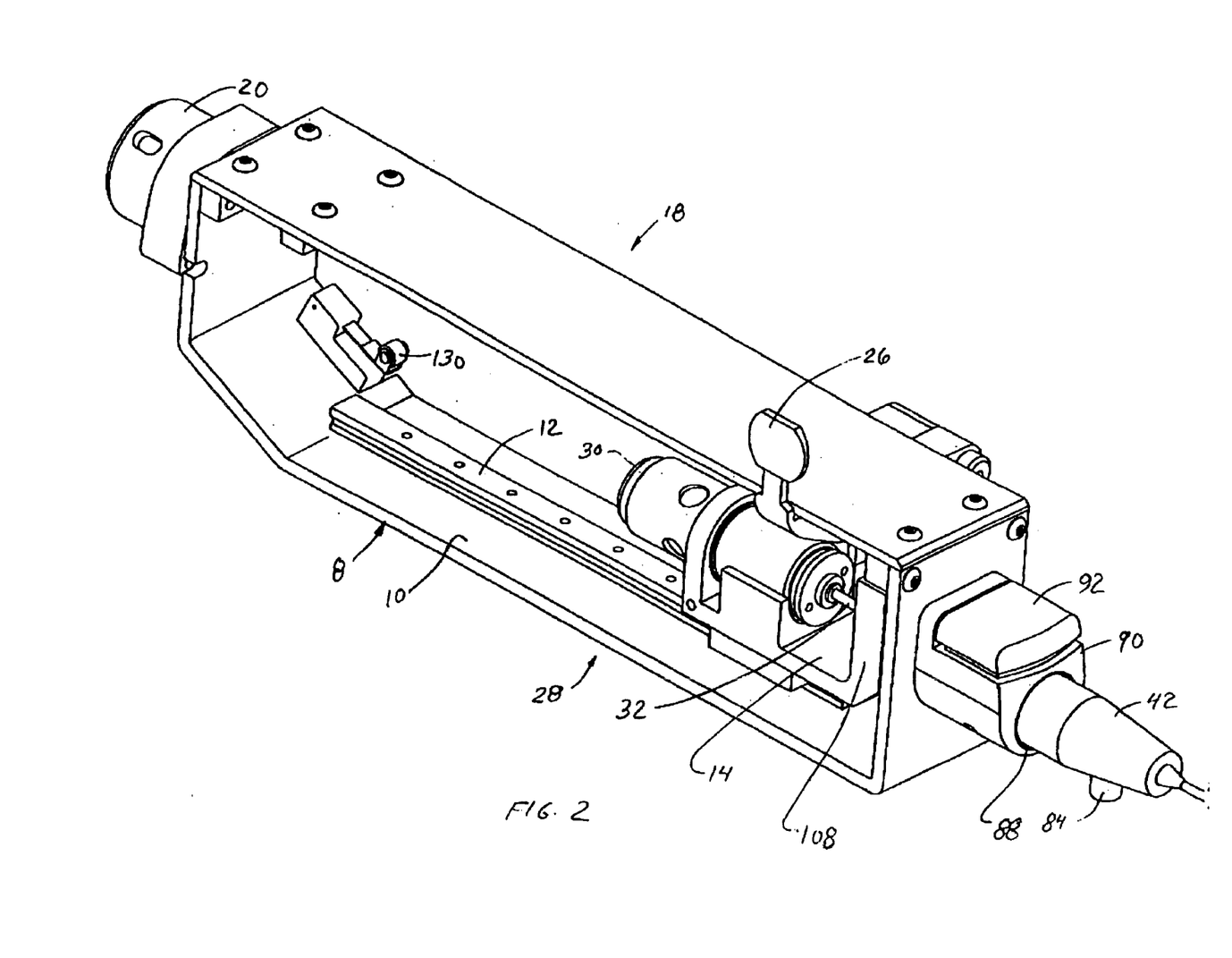
FIG. 2 is a perspective view of a prototype of the drive assembly and the proximal portion of the catheter assembly of FIG. 1 with the drive assembly in a distal, extended position and with the sides of the body of the drive assembly removed for convenient access.
Figure 2A:
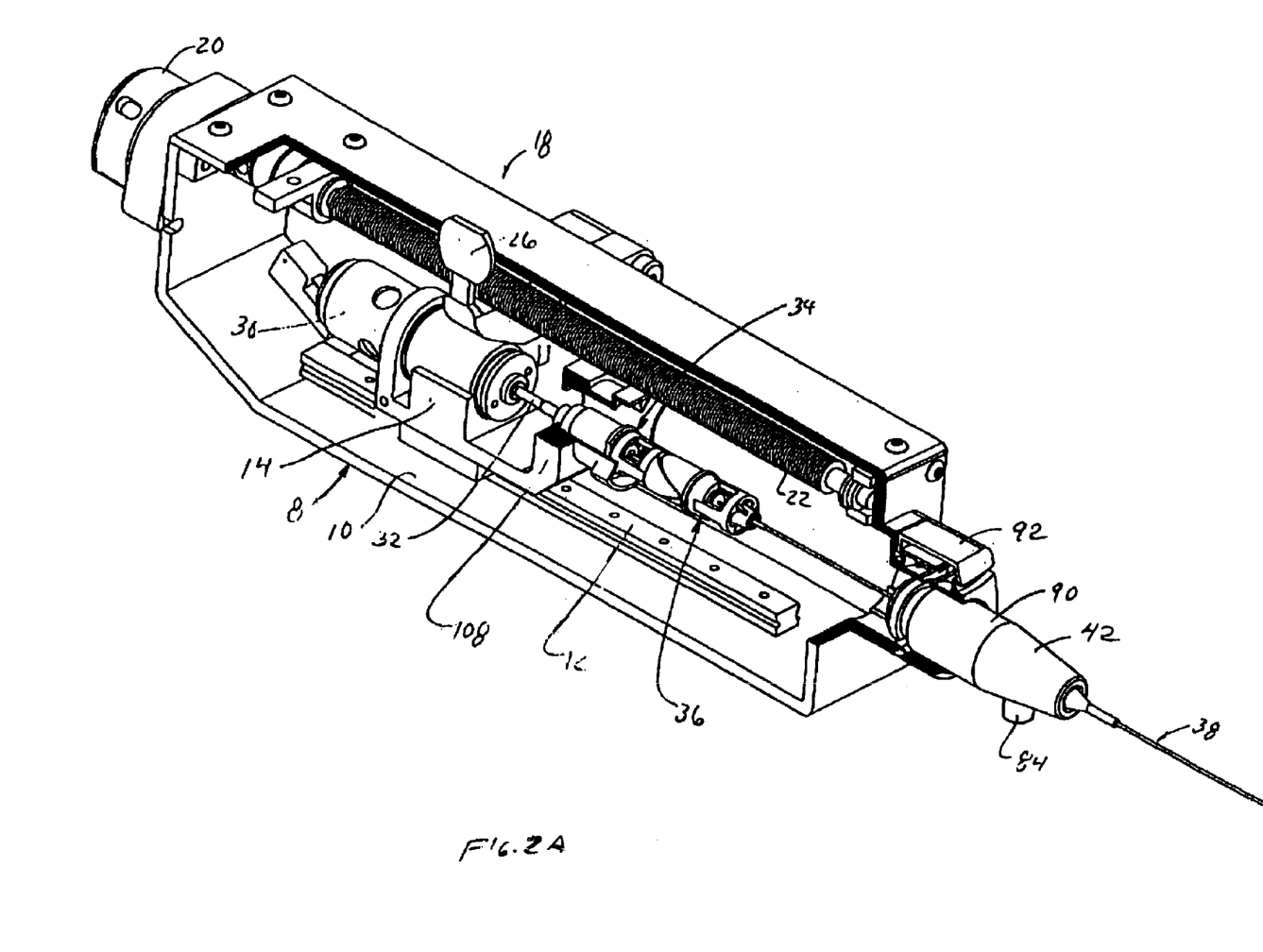
FIG. 2A is similar to FIG. 2 with the drive assembly in a proximal, pulled-back or retracted position.

FIG. 1 illustrates, in schematic form, a catheter system 2 including a drive assembly 4 to which a typically disposable catheter assembly 6 is removably mounted. Referring now also to FIGS. 2 and 2A, drive assembly 4 includes a body 8 having a base 10 supporting a linear bearing track 12. A drive chassis 14 is mounted for linear movement along a longitudinal path 16 by a longitudinal driver 18. Longitudinal driver 18 includes a longitudinal drive motor 20 which rotates a longitudinal drive screw 22 rotatably supported at each end by body 8. Driver 18 also includes a threaded clamp 24 having threads which match the threads on drive screw 22. Clamp 24 is mounted to and moves with drive chassis 14. Clamp 24 is normally biased into engagement with drive screw 22, but can be moved out of engagement with drive shaft 22 by the user moving a drive clamp handle 26; doing so disengages clamp 24 from drive screw 22 and permits the user to move drive chassis 14 along longitudinal path 16. Releasing drive clamp handle 26 allows clamp 24 to again engage drive screw 22; this secures drive chassis 14 in position along longitudinal path 16, subject to any subsequent rotation of drive screw 22.

Drive assembly 4 also includes a rotary driver 28 mounted to and carried by drive chassis 14. Rotary driver 28 includes a rotary drive motor 30, mounted to drive chassis 14, which rotates a drive shaft 32. As will be discussed in more detail below, drive shaft 32 rotates a first combined connector 34. First combined connector 34 moves with drive chassis 14 along longitudinal path 16. First combined connector 34 operably engages a second combined connector 36, also discussed below, the second combined connector being a part of catheter assembly 6.

Figure 3:
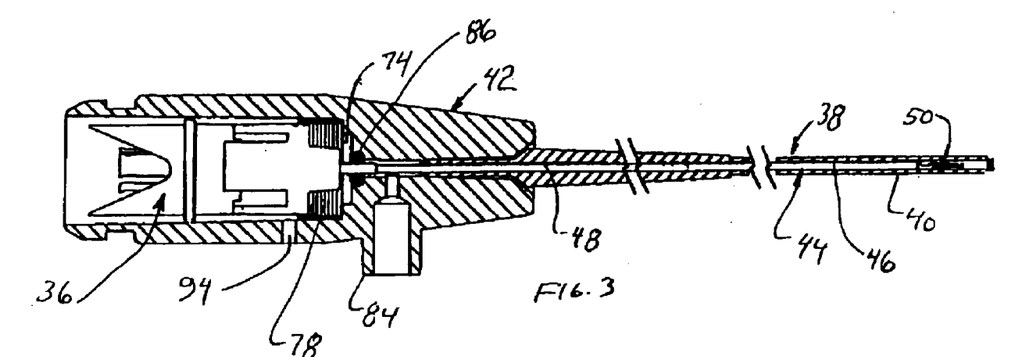
FIG. 3 is a partial cross-sectional view of the catheter assembly of FIGS. 1 and 2 with the cable assembly in a distal position, the bellows collapsed and the imaging element at the tip of the sheath.
Figure 3A:
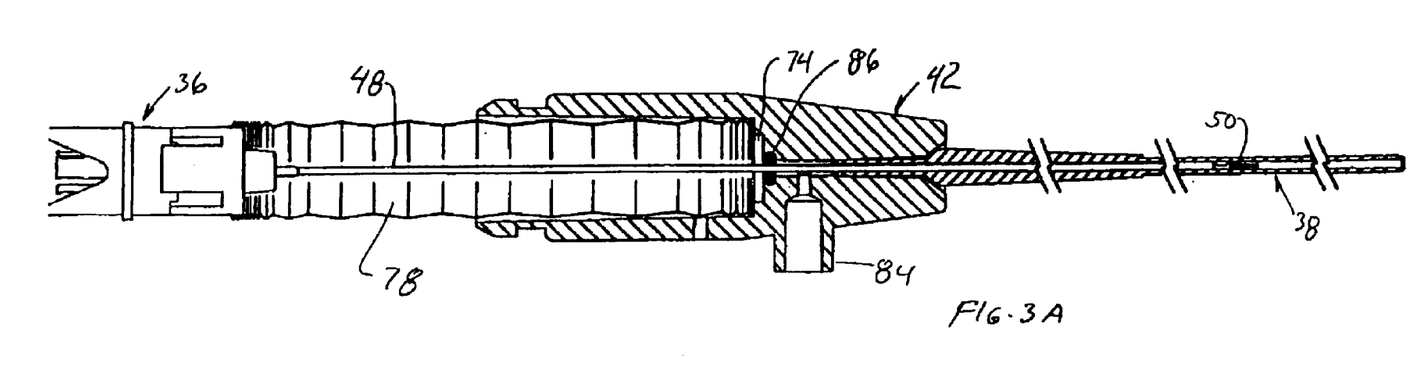
FIG. 3A is a view similar to FIG. 3 with the cable assembly in the proximal position of FIG. 2A, the bellows expanded and the imaging element pulled back away from the tip of the sheath.
Figure 4:
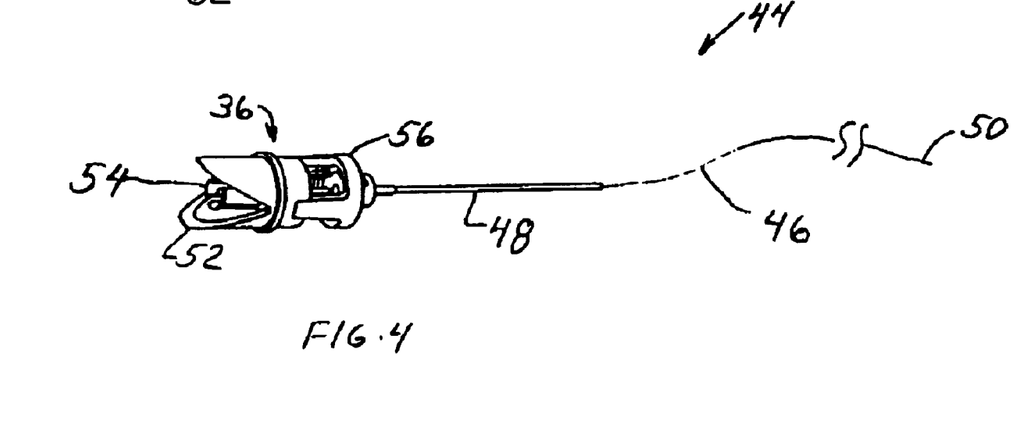
FIG. 4 is an isometric view of the cable assembly of FIG. 3.
Figure 5:
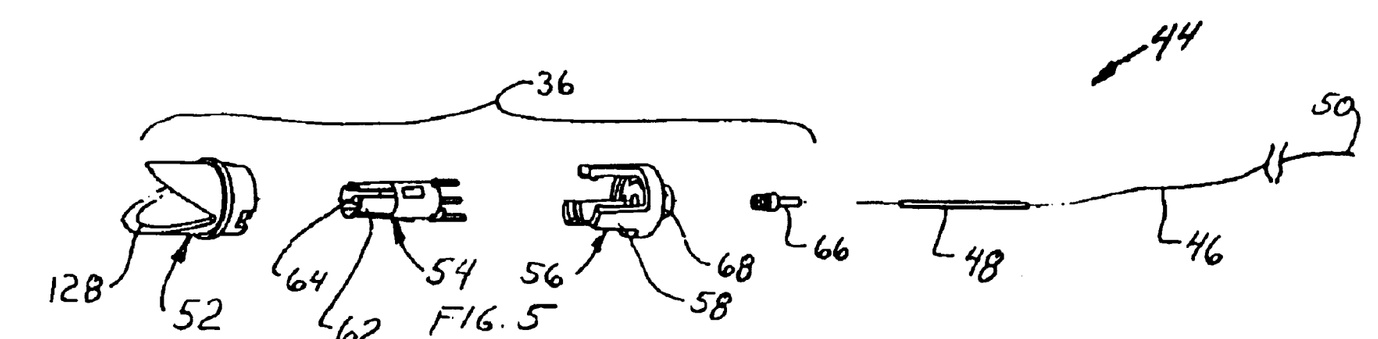
FIG. 5 is an exploded isometric view of the cable assembly of FIG. 4.

Turning now to FIGS. 3–5, catheter assembly 6 will be described in more detail. Catheter assembly 6 includes a hollow sheath 38 extending between a tip 40 at its distal end and a hub 42 at its proximal end with a main portion 43 in between. Sheath 38 houses a cable assembly 44, see FIGS. 4 and 5. Cable assembly 44 includes second combined connector 36 from which a cable 46 (the elongate operative element) extends. Cable 46 includes a stiff initial section 48 extending from second combined connector 36 and an image element 50 at the distal end of cable 46. Stiff initial section 48 is typically made by securing a length of hypotube (a thin-walled stainless steel tube) over the proximal end of the cable. Cable assembly 44 can be used for ultrasonic imaging, laser imaging or other imaging purposes. Also, cable assembly 44 could be used for purposes other than imaging such as ablation, photodynamic therapy, delivery of therapeutic or diagnostic fluids, delivery of devices such as stents, and for other purposes. In the preferred embodiment, tip 40 is open to permit fluid to be flushed through the interior of sheath 44; in some situations tip 40 may be sealed. In some cases image element 50 may be positioned past tip 40 and external of sheath 38.

Second combined connector 36 includes a second rotary drive connector 52 and a second electrical connector or plug 54 (a data/information connector). A drive joint 56 has three spring fingers 58 which engage recesses 60 formed in drive connector 52 to secure plug 54 in place. Plug 54 has spring finger electrical contacts 62 surrounding a center pin 64. Initial section 48 of cable 46 is secured to the interior of a rotary shaft coupler 66, coupler 66 being affixed to a hub portion 68 of drive joint 56. Appropriate electrical connections between drive cable 46 and plug 54 are made in a conventional manner.

Hub 42 of sheath 38 includes a main cavity 70 which houses second combined connector 36. Catheter assembly 6 also includes a bearing washer 74 mounted between second combined connector 36 and the proximal end of main cavity 70. Bellows 78, typically made of polyester shrink (?) or PTFE, is fastened at its proximal edge 80 to drive joint 56 and its distal edge 82 to hub 42. Bellows 78 is used to help prevent contamination of the interior of sheath 38. Bearing washer 74, used to secure the distal end of a bellows 78 to hub 42, is made of a low friction polymer.

Hub 42 also includes a fluid or flush port 84 coupled to the interior of sheath 38 to permit the sheath interior to be flushed with a saline solution or other suitable fluid. An O-ring fluid seal 86 is used between hub 42 and coupler 66 (in position of FIG. 2) or stiff initial section 48 (in position of FIG. 2A) to prevent the flow of fluid from flush port 84 back into cavity 70 and thus into the interior of drive assembly 4.

Catheter assembly 6 is quickly and easily mounted to drive assembly 4. To do so, the proximal end of hub 42 is inserted into a through-hole 88 formed in a proximal portion mount 90 of body 8 of drive assembly 4 until latched into place. This occurs by the engagement of an upwardly-extending, spring-biased latch pin, not shown, engaging a recess 94 formed in hub 42; the latch pin can be removed from recess 94 by the user pressing on a release button 92. Mounting catheter assembly 6 to drive assembly 4 preferably occurs when rotary driver 28 is in the distal-most or fully-extended position of FIGS. 1 and 2. Upon mounting hub 42 into proximal portion member 90, second combined connector 36 automatically blind matably connects with first combined connector 34 to provide for longitudinal and rotational driving connection and for electrical connection.

Figure 6:
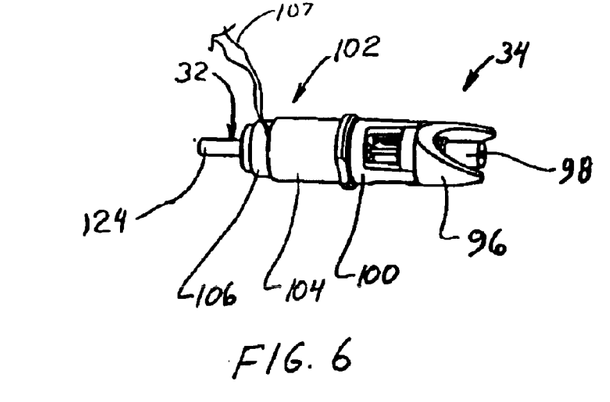
FIG. 6 is an isometric view of the first combined connector and bearing assembly of FIG. 1.
Figure 7:
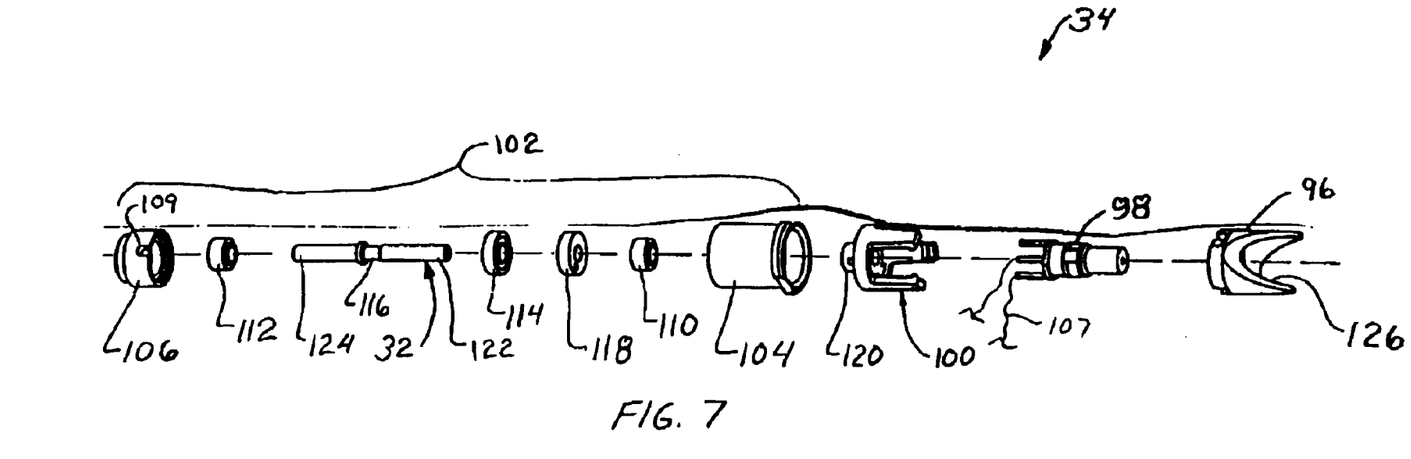
FIG. 7 is an exploded isometric view of the first combined connector and bearing assembly of FIG. 6.

Turning now to FIGS. 6 and 7, first combined connector assembly 34 will be discussed. First combined connector assembly 34 includes a first rotary drive connector 96 configured for complementary mating engagement with second rotary drive connector 52. Assembly 34 also includes a first electrical connector or socket 98 secured between connector 96 and a second drive joint 100. Socket 98 and plug 54 are configured to mate with one another in a coaxial mating arrangement in a manner similar to connector 22, electrical connector 54 and drive joint 56 of FIG. 5. First combined connector 34 is coupled to a bearing assembly 102. Bearing assembly 102 includes first and second housing portions 104, 106 which house drive shaft 32. Electrical wires 107 extend from socket 98, through housing portion 104, and through a cut-out 109 in housing portion 106 for connection to appropriate circuitry, not shown. Bearing assembly 102 is supported by the front end 108 of drive chassis 14 engaging housing portion 104. Drive shaft 32 is supported within housing portions 104, 106 by a pair of bearings 110, 112. Drive shaft 32 passes freely through a non-rotating ferrite 114 which is fixed within distal housing portion 104, typically through a light press fit or through the use of an adhesive. Non-rotating ferrite 114 is positioned at a necked down portion 116 of drive shaft 108. A rotating ferrite 118 is mounted to drive shaft 32 to be positioned adjacent to non-rotating ferrite 114. Rotating ferrite 118 is secured to drive shaft 32, such as through a light press fit, and rotates with the drive shaft. Rotating and non-rotating ferrites 118, 114 are used to monitor the rotation of drive shaft 32 and, thus, of cable assembly 44.

The hub portion 120 of drive joint 100 is housed within the distal end of distal housing portion 104. The distal end 122 of drive shaft 32 is keyed or otherwise fixed to hub portion 120 so that rotating drive shaft 32 causes first rotary drive connector 96 to rotate, thus rotating cable assembly 44. The proximal end 124 of drive shaft 32 extends beyond housing portion 106 and into driven engagement with rotary drive motor 30. Thus, rotary motion of rotary drive motor 30 causes drive shaft 32 to rotate, thus rotating cable assembly 44. Longitudinal movement of drive chassis 14 through the engagement of clamp 24 with drive screw 22 causes rotary driver 28 to move along longitudinal path 16. However, the frictional connection between plug 54 and socket 98 causes cable assembly 44, see FIG. 4, to be pulled along longitudinal path 16 with the longitudinal movement of rotary driver 28. The use of stiffened section 48 as the initial portion of cable 46 provides the necessary support for the cable during this longitudinal movement.

In use, an appropriate catheter assembly 6 is selected to be used during a procedure. If rotary driver 28 is not in its distal-most position of FIGS. 1 and 2, the user will place rotary driver 28 at its distal-most position, typically by grasping drive clamp handle 26, temporarily disengaging clamp 24 from drive screw 22, and then manually moving the rotary driver in the distal direction to its distal-most position. Once in position, drive clamp handle 26 is released, permitting the reengagement of threaded clamp 24 with drive screw 22, thus securing rotary driver 28 in place. Spring biased release button 92 is then depressed and the proximal end of hub 42 is inserted into through-hole 88 formed in proximal portion mount 90. Once hub 42 is partially inserted, release button 92 is released and hub 42 is continued to be inserted into mount 90 until the locking pin attached to release button 92 engages recess 94 formed in hub 42. When this occurs, hub 42 becomes properly secured to drive assembly 4.

During this insertion, first and second combined connectors 34, 36 blind matably connect to one another. First and second rotary drive connectors 96, 52 have alignment/drive surfaces 126, 128 which extend both circumferentially and longitudinally so to provide the proper rotary orientation upon engagement of the connectors. In addition, plug 54 and socket 98 are axially aligned during this movement and become electrically coupled to one another as the first and second rotary drive connectors 96, 52 mate.

Tip 40 of catheter assembly 6 is then transluminally positioned to the target area within the patient. With rotary driver 28 in its distal-most position, which causes imaging element 50 to be in its distal-most position, rotary drive motor 30 and longitudinal drive motor 20 can be simultaneously or sequentially actuated to permit 360° images to be obtained along a length of vessel or other cavity within a patient. Excessive proximal movement is prevented when drive chassis 14 engages a limit switch 130 mounted to body 8.

The movements of imaging element 50 are controlled in a very stable manner through the use of motors 20, 30 to provide superior imaging than could otherwise be obtained. If desired, rotary driver 28 can be manually longitudinally positioned through the disengagement of clamp 24, the manual movement of rotary actuator 28 along longitudinal path 16 and the reengagement of clamp 24 with drive screw 22. In the preferred embodiment, the length of longitudinal travel will be about 10 cm. Drive assembly 4 can be made to accommodate other lengths of longitudinal travel as well.

Modification and variation can be made to the disclosed embodiment without departing from the subject of the invention as defined in the following claims. For example, other types of rotary and longitudinal drivers could be used, such as a longitudinal chain or belt drive in lieu of the longitudinal drive screw 22. It is desirable that combined connectors 34, 36 be engagable and disengagable by straight longitudinal movement of the connectors into and out of engagement. However, in appropriate circumstances, a type of twist-lock blind matable connector may be used as well. Alignment/drive surfaces 126, 128 are basically dual V-shaped surfaces so that cable assembly 44 ends up at one of two different rotary orientations, 180° apart, relative to the rotary orientation of first combined connector 34. It may be desirable in some circumstances to ensure only a single relative rotary orientation of connectors 34, 36. This could be achieved by having a single angled surface for guiding the connectors into the proper rotary orientation and separate rotary drive surfaces for a rotary driving engagement between the two connectors. Body 8 is shown in a very simple form. In a commercial embodiment, body 8 would preferably have a more ergonomic shape, and may have fixed or extendable legs to allow drive assembly to rest comfortably but securely on, for example, the patient's leg or chest. While it is expected that drive assembly 4 will be connected to remote power and control assemblies, it may be desirable to include a controller, input panel, and a battery pack as a part of drive assembly 4 to make the drive assembly substantially self-contained. Data from catheter system 2 could be then provided to an external recorder and/or monitor through hardwire or telemetry, such as by using radio frequency transmitters and receivers. While the invention is particularly adapted for imaging of vascular regions, the invention is suitable types of diagnostic and therapeutic procedures in vascular and other body structures. Instead of bellows 78, other structures, such as telescoping tubing, can be used to help prevent contamination of the interior of sheath 38; the bellows or tubing could have round, rectangular or other cross-sectioned shapes.

Any and all patents, applications and publications referred to above are incorporated by reference.

What is claimed is:

1. A catheter assembly comprising:
    a hollow sheath having a proximal portion, a tip, and a hub at the proximal portion;
    an elongate operative element slidably and rotatably housed within the sheath, the operative element comprising a distal end and a proximal end;
    the elongate operative element comprising a relatively stiff initial section extending from the proximal end thereof, wherein the stiff initial section extends distally beyond the hub to permit the elongate operative element to move back and forth within the hollow sheath;
    a rotatable combined connector secured to the proximal end of the operative element so as to be proximal to the hub, said combined connector comprising a data/information connector and a mechanical connector; and said combined connector comprising an angled rotary alignment surface that is adapted to blind mate with a corresponding connector of a drive unit that has an angled rotary alignment surface.

2. The catheter assembly according to claim 1 wherein said data/information connector comprises an electrical connector.

3. The catheter assembly according to claim 1 wherein said mechanical connector comprises a rotary drive connector.

4. The catheter assembly according to claim 3 wherein said rotary drive connector comprises a drive surface which simultaneously extends axially and circumferentially.

5. The catheter assembly according to claim 1 wherein said combined connector comprises a rotary alignment surface.

6. The catheter assembly according to claim 1 wherein said elongate operative element comprises an imaging cable having an image element at said distal end thereof.

7. The catheter assembly according to claim 1 wherein said initial section comprises a metal tube.

8. The catheter assembly according to claim 1 further comprising a fluid seal between said proximal portion of said sheath and the initial section of the elongate operative element.

9. The catheter system according to claim 1 wherein said elongate operative element comprises a flexible imaging core and a relatively stiff tube at the proximal end thereof to create a relatively stiff initial section of the elongate operative element extending from the proximal end thereof.

* * * * *